(12) United States Patent
Tohda et al.

(10) Patent No.: US 10,660,935 B2
(45) Date of Patent: May 26, 2020

(54) METHODS FOR AMELIORATING MEMORY IMPAIRMENT IN A MEMORY DISORDER CAUSED BY NEURONAL CELL DEATH OR ABETA AGGREGATION USING A PEPTIDE

(71) Applicants: JAPAN BIO PRODUCTS Co., Ltd., Shibuya-ku, Tokyo (JP); National University Corporation University of Toyama, Toyama-shi, Toyama (JP)

(72) Inventors: Chihiro Tohda, Toyama (JP); Taiichi Kaku, Tokyo (JP); Hiroyuki Miyazaki, Tokyo (JP)

(73) Assignees: JAPAN BIO PRODUCTS Co., Ltd., Tokyo (JP); National University Corporation University of Toyama, Toyama-shi (JP)

( * ) Notice: Subject to any disclaimer, the term of this patent is extended or adjusted under 35 U.S.C. 154(b) by 0 days.

(21) Appl. No.: 16/483,515

(22) PCT Filed: Aug. 18, 2017

(86) PCT No.: PCT/JP2017/029598
§ 371 (c)(1),
(2) Date: Aug. 5, 2019

(87) PCT Pub. No.: WO2018/150609
PCT Pub. Date: Aug. 23, 2018

(65) Prior Publication Data
US 2019/0358287 A1 Nov. 28, 2019

(30) Foreign Application Priority Data
Feb. 14, 2017 (JP) .................. 2017-024946

(51) Int. Cl.
| | | |
|---|---|---|
| *A61K 38/00* | (2006.01) | |
| *A61K 38/18* | (2006.01) | |
| *C07K 7/00* | (2006.01) | |
| *A61K 49/00* | (2006.01) | |
| *A61B 5/00* | (2006.01) | |
| *A61K 38/17* | (2006.01) | |
| *A61K 38/08* | (2019.01) | |
| *A61P 25/28* | (2006.01) | |
| *G01N 33/50* | (2006.01) | |
| *G01N 33/68* | (2006.01) | |

(52) U.S. Cl.
CPC .............. *A61K 38/08* (2013.01); *A61P 25/28* (2018.01); *A01K 2267/03* (2013.01); *A61B 5/4088* (2013.01); *A61B 5/4833* (2013.01); *A61K 2300/00* (2013.01); *C07K 2319/00* (2013.01); *G01N 33/5088* (2013.01); *G01N 33/6896* (2013.01); *G01N 2333/4709* (2013.01); *G01N 2800/28* (2013.01); *G01N 2800/2814* (2013.01); *G01N 2800/2821* (2013.01); *G01N 2800/30* (2013.01); *G01N 2800/52* (2013.01); *G01N 2800/56* (2013.01)

(58) Field of Classification Search
CPC ....... G01N 2800/2821; G01N 33/6896; G01N 2333/4709; A61K 2300/00; A01K 2267/03; C07K 2319/00
See application file for complete search history.

(56) References Cited

U.S. PATENT DOCUMENTS

| | | | |
|---|---|---|---|
| 8,940,789 B2 * | 1/2015 | Kusano ................ | A61K 31/352 435/125 |
| 9,102,666 B2 * | 8/2015 | Roses ................ | A61K 31/4439 |
| 2010/0047170 A1 * | 2/2010 | Denmeade ............ | C07K 14/47 424/9.1 |
| 2010/0151096 A1 * | 6/2010 | Damodaran ............ | A23G 9/38 426/327 |
| 2011/0065645 A1 | 3/2011 | Zou | |
| 2012/0283166 A1 * | 11/2012 | Denmeade ............ | C07K 14/47 514/1.3 |
| 2015/0065391 A1 * | 3/2015 | Mischak ............ | G01N 33/6848 506/12 |

FOREIGN PATENT DOCUMENTS

| | | |
|---|---|---|
| JP | 2010104364 A | 5/2010 |
| WO | 03028543 A2 | 4/2003 |
| WO | 2007139120 A1 | 12/2007 |
| WO | 2012096873 A1 | 7/2012 |

OTHER PUBLICATIONS

Matthews, Memory Dysfunction, Continuum, 2015; 21:613-626.*
Sun et al. Trends in Pharmacol. Sci. 2015; 36: 384-394.*
JP2010-104364—English translated version, Taiji et al., published May 13, 2010.*
Anger. Neurotoxicology 1991. 12: 403-13.*
Tayebati. Mech. Ageing Dev. 2006. 127: 100-8.*
Sarter. Neurosci. and Biobehav. Rev. 2004. 28: 645-650.*
Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Kakoi, C, et al. Collagen peptides enhance hippocampal neurogenesis and reduce anxiety-related behavior in mice, (2012), Biomedical Research, vol. 33, pp. 273-279, 7 pages.
Higashida, C, et al. Memory Dysfunction Ameliorating Action in Model Mouse with Alzheimer's Disease by Human Placenta-Derived Drug Laennec, (2016), Japanese Society of Biological Psychiatry, p. 61, 3 pages.

\* cited by examiner

*Primary Examiner* — Chang-Yu Wang
(74) *Attorney, Agent, or Firm* — Hunton Andrews Kurth LLP

(57) ABSTRACT

A peptide consisting of an amino acid sequence of GPPG-PAG (SEQ ID NO: 1) is disclosed. According to the present invention, a novel compound for improving memory disorder is provided.

2 Claims, 3 Drawing Sheets

Specification includes a Sequence Listing.

METHODS FOR AMELIORATING MEMORY IMPAIRMENT IN A MEMORY DISORDER CAUSED BY NEURONAL CELL DEATH OR ABETA AGGREGATION USING A PEPTIDE

CROSS-REFERENCE TO RELATED APPLICATIONS

This application is a national phase application based on International Patent Application No. PCT/JP2017/029598 filed Aug. 18, 2017, claiming priority to Japanese Patent Application No. 2017-024946 filed Feb. 14, 2017, the entire contents of which both are incorporated herein by reference.

TECHNICAL FIELD

The present invention relates to a compound for ameliorating memory disorder.

BACKGROUND ART

As compounds for ameliorating memory disorder including Alzheimer's disease and dementia and the like, 4'-demethyl nobiletin and 4'-demethyl tangeretin (Patent Literature 1) as well as low-dose pioglitazone (Patent Literature 2) and the like have been known.

CITATION LIST

Patent Literature

Patent Literature 1: U.S. Pat. No. 8,940,789
Patent Literature 2: International Publication No. WO 12/096873

The instant application contains a Sequence Listing which has been submitted via EFS-Web and is hereby incorporated by reference in its entirety. The ASCII text tile, created on Jul. 30, 2019, is named FP17-0523-00US-XX_Sequence_Listing_75447408_1.txt, and is 1,034 bytes in size.

SUMMARY OF INVENTION

Technical Problem

An object of the present invention is to provide a novel compound for ameliorating memory disorder.

Solution to Problem

The inventors of the present invention found that a peptide consisting of an amino acid sequence GPPGPAG (SEQ ID NO: 1) ameliorates memory disorder, and achieved to complete the present invention.

Namely, the present invention provides the following [1] to [6].
[1] A peptide consisting of an amino acid sequence of SEQ ID NO: 1.
[2] A nucleic acid encoding a peptide according to [1].
[3] A pharmaceutical composition for ameliorating memory disorder, comprising a peptide according to [1].
[4] A method of ameliorating memory disorder, comprising administering a pharmaceutical composition comprising a peptide consisting of an amino acid sequence of SEQ ID NO: 1 to a subject in need thereof.
[5] A peptide consisting of an amino acid sequence of SEQ ID NO: 1 for a method of ameliorating memory disorder.
[6] Use of a peptide consisting of an amino acid sequence of SEQ ID NO: 1 for manufacturing a pharmaceutical composition for ameliorating memory disorder.

Advantageous Effects of Invention

According to the present invention, a novel compound for ameliorating memory disorder was provided.

DESCRIPTION OF EMBODIMENTS

Figure 1:
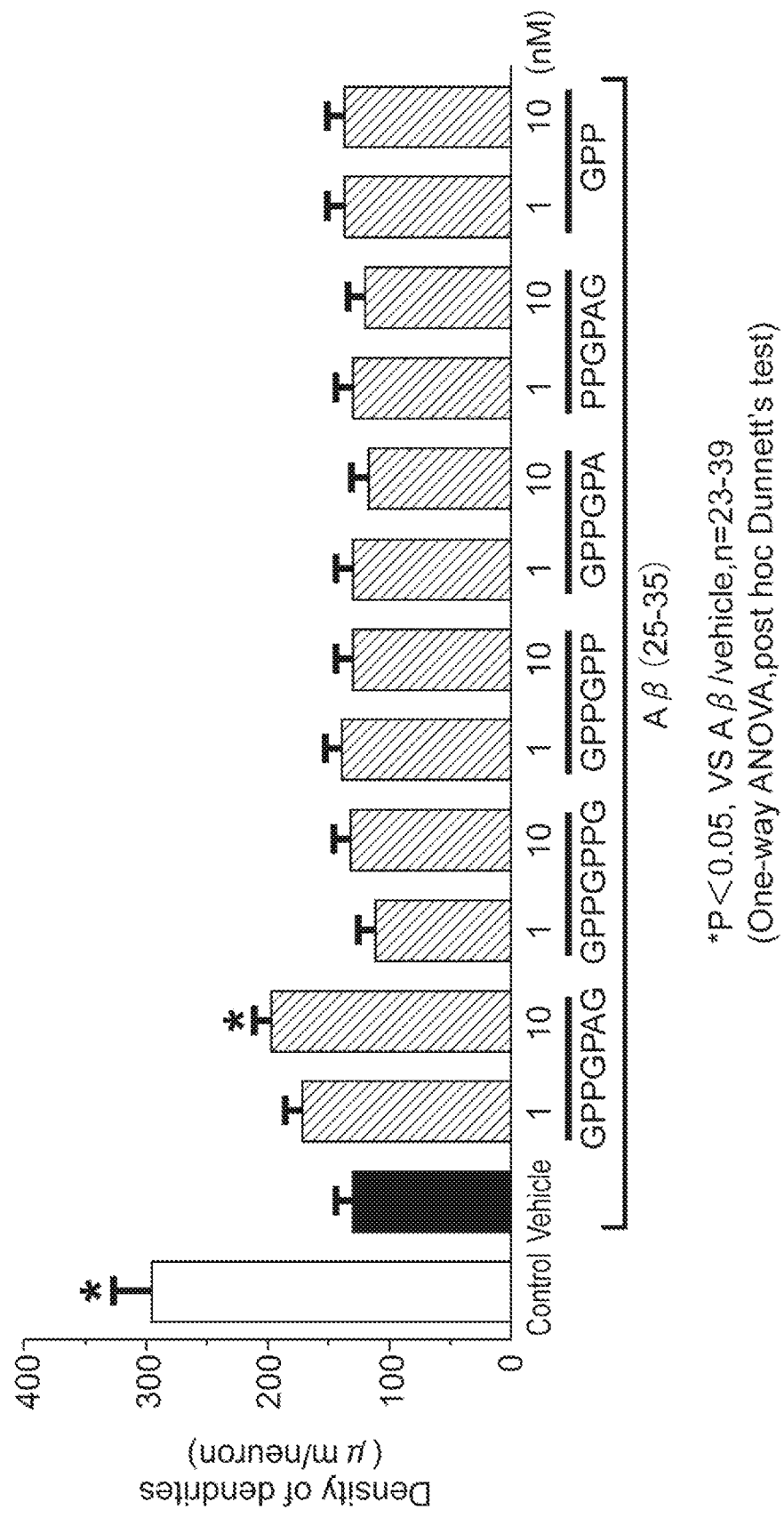
FIG. 1 is a diagram showing a change in density of dendrites with posttreatment with 1 nM and 10 nM of GPPGPAG (SEQ ID NO: 1), GPPGPPG (SEQ ID NO: 2), GPPGPP (SEQ ID NO: 3), GPPGPA (SEQ ID NO: 4), PPGPAG (SEQ ID NO: 5), and GPP in Aβ25-35-treated cells. "Control" indicates Aβ25-35 untreated cells, and "Vehicle" indicates Aβ25-35-treated cells treated with a simple solvent without the peptide. Asterisks indicate significant differences (*P<0.05).

Preferred embodiments of the present invention will be described in detail below. However, the present invention is not limited to these embodiments.

The peptide of the present invention consists of an amino acid sequence of SEQ ID NO: 1, and can be synthesized by methods well-known to those skilled in the art such as a peptide solid-phase synthesis method and a peptide liquid-phase synthesis method. A nucleic acid encoding the peptide consisting of the amino acid sequence of SEQ ID NO: 1 can also be synthesized by methods well-known to those skilled in the art such as a solid-phase synthesis method. The peptide consisting of the amino acid sequence of SEQ ID NO: 1 can be expressed and obtained using the nucleic acid by methods well-known to those skilled in the art such as a method using an expression system with E. coli, yeast, insect cells-baculovirus, or the like.

In one embodiment of the present invention, the peptide consisting of the amino acid sequence of SEQ ID NO: 1 can be formulated into a pharmaceutical composition by a known formulation method. The content of the peptide in the pharmaceutical composition can be appropriately determined by one skilled in the art depending on the form of the pharmaceutical composition, disease state and body weight and the like of a subject to be applied with the pharmaceutical composition. The pharmaceutical composition can contain the peptide, and an appropriate ingredient required for drug manufacturing such as a pharmacologically acceptable carrier or vehicle and an additive. Examples of carriers or vehicles include sterilized purified water and saline.

Examples of additives include excipients, pH adjusters, stabilizers, thickeners, preservatives, surfactants, emulsifiers, and diluents. The types and contents of ingredients required for drug manufacturing such as a pharmacologically acceptable carrier or vehicle and an additive can be appropriately adjusted depending on the form of the pharmaceutical composition.

In one embodiment of the present invention, the pharmaceutical composition comprising the peptide consisting of the amino acid sequence of SEQ ID NO: 1 can be administered to a subject in need thereof.

A subject in need thereof means a subject developing memory disorder. Memory disorder includes a memory disorder due to neural cell dysfunction or neural cell death within the brain. Therefore, a subject in need thereof may be a subject developing memory disorder due to neural cell dysfunction or neural cell death within the brain. Memory disorder also includes Alzheimer's disease and dementia. Therefore, a subject in need thereof may be a subject developing Alzheimer's disease or dementia. A subject is a mammal including a human and a non-human animal, and it is preferable that a human be a subject.

Examples of route of administration of the pharmaceutical composition include oral administration, transnasal administration, transmucosal administration, intradermal administration, subcutaneous administration, transdermal administration, intravenous administration, intramuscular administration, intraperitoneal administration, intraarterial administration, intraventricular administration, subarachnoid administration, and epidural administration.

A form of the pharmaceutical composition can be appropriately selected depending on a route of administration, and exemplarily includes an aqueous solution, syrup, jelly, tablets, capsules, granule, and powder.

An effective dosage and administration schedule of the pharmaceutical composition can be appropriately determined from a route of administration, disease state, body weight, and age of a subject, or the like, by one skilled in the art.

A pharmaceutical composition in one embodiment of the present invention can be used as a therapeutic drug for memory disorder including Alzheimer's disease and dementia and the like, and can also be used as a therapeutic drug for Alzheimer's disease and dementia. Therapy means not only completely restoring a subject developing memory disorder, but also includes ameliorating memory disorder and suppressing progression of memory disorder.

EXAMPLES

[Alzheimer's Disease Model Mice]

Alzheimer's disease model mice: Transgenic mice that are animal models for Alzheimer's disease (5XFAD) were obtained from the Jackson Laboratories (Bar Harbor, Me., USA). 5XFAD mice overexpress human APP695 cDNA having mutations of Swedish (K670N and M671L), Florida (I716V), and London (V717I), and human PS1 cDNA (mutations at M146L and L286V) under transcriptional control of the neuron-specific murine Thy-1 promoter (Oakley, H. et al., J Neurosci, 26, 10129-10140, 2006). Those were maintained by crossing B6/SJL F1 breeders with hemizygous transgenic mice.

In the Example, 5XFAD mice was 5-7-month-old females for use, and raised at 22±2° C. with a humidity of 50±5% in condition of voluntary intake of food and water under environment controlled with 12-hour light-dark cycle starting from 7 a.m.

[Peptides]

Peptides used in the Example are shown in Table 1. The peptides were dissolved in sterilized purified water for experiments of cultured neural cells, and in artificial cerebrospinal fluid (ACSF: 130 mM NaCl, 24 mM $NaHCO_3$, 3.5 mM KCl, 1.3 mM $NaH_2PO_4$, 2 mM $CaCl_2$, 2 mM $MgCl_2.6H_2O$ and 10 mM glucose at pH 7.4) for experiments of intraventicular administration in mice.

TABLE 1

| Amino acid sequence | SEQ ID NO |
|---|---|
| GPPGPAG | 1 |
| GPPGPPG | 2 |
| GPPGPP | 3 |
| GPPGPA | 4 |
| PPGPAG | 5 |
| GPP | — |

[Statistical Processing]

In the Example, the results obtained are subject to the following statistical processing:

One-way analysis of variance (one-way ANOVA), Dunnett's posthoc test, unpaired t-test, and paired t-test were performed using GraphPad 5 (Graphpad Prism 6) (GraphPad Software Co., La Jolla, Calif., USA). *$P<0.05$, **$P<0.01$ and #$P<0.05$ is considered as statistically significant, and averages are shown with standard errors.

[Quantitative Experiment for Dendritic Elongation]

Murine cerebral cortical neural cells were prepared by the following method. Fetuses extracted from a 14-day postnatal ddY mouse (Japan SLC, Shizuoka) were washed with PBS, then decapitated, and added in a medium made for primary culture [12% equine serum (Life Technologies), 2 mM L-glutamic acid, and 0.6% glucose dissolved in Neurobasal media (Life Technologies, Carlsbad, Calif., USA)]. Only cerebral cortex was isolated in the medium under a stereomicroscope (SZ-61, Olympus, Tokyo).

Cerebral cortex was cut into about 1 mm-sized cubes in a safety cabinet. Centrifugation was performed at 700 rpm for 3 minutes, then the supernatant was removed, and to the precipitate was added 2 mL of 0.05% trypsin-0.53 mM EDTA solution (Life Technologies) to make a suspension. The suspension was incubated at 37° C. for 15 minutes with stirring for every 5 minutes, loaded with 4 mL of the medium, centrifuged at 700 rpm for 3 minutes to remove the supernatant, and to the precipitate was added 2 mL of 600 U/mL DNase I (Wako Pure Chemical Co., Ltd)-0.03% trypsin inhibitor (Life Technologies)-PBS solution to make a suspension.

The suspension was further incubated at 37° C. for 15 minutes with stirring for every 5 minutes, loaded with 4 mL of the medium, and centrifuged at 700 rpm for 3 minutes. The sediment was loaded with 4 mL of a calcium-magnesium-free Hank's balanced salt solution (HBSS), and centrifuged at 700 rpm for 3 minutes. 4 mL of the medium was added to the sediment.

The sediment loaded with the medium was gently suspended with a Pasteur pipette in which its tip had been heated and smoothed, until the cell clumps were invisible, and then filtrated with a 70 μm nylon cell strainer (Falcon, N.J., USA). Cell culture was performed in an 8-well chamber slide (falcon). Cells were seeded into the one coated the day before [in which Poly-D-Lysine (PDL, Wako Pure Chemical Co., Ltd) diluted with PBS to 0.005 mg/mL was plated and incubated at 37° C.; on the day of culture, it was washed twice with sterilized purified water.] Culture was started at 37° C. and 10% $CO_2$ under saturated vapor.

In quantitative experiment for dendritic elongation, the medium was all changed with a fresh medium containing B-27 supplement (Invitrogen) instead of equine serum 5 hours and 3 days after start of culture. At medium change after 3 days, the pre-aggregated partial sequence fragment of amyloid beta (Aβ25-35) was added up to 10 μM. After another 3 days, each peptide or solvent was added when the medium was all changed into a fresh one, and after another 4 days, immunostaining was performed.

Immunostaining for quantifying dendritic elongation was performed as follows. After the end of the drug treatment term, the medium was removed and the cells were washed with PBS, added with 4% paraformaldehyde (PFA, Wako Pure Chemical Co., Ltd)-PBS solution, left standing at room temperature for an hour, and fixed. Wash with 0.3% triton X-100 (Wako Pure Chemical Co., Ltd)-PBS solution for 5 minutes was performed twice. Then, a primary antibody solution (0.3% triton X-100-PBS solution, 1% normal goat serum [Wako Pure Chemical Co., Ltd], a primary antibody) was added, and reacted at 4° C. overnight.

For the primary antibody, rabbit anti-MAP2 polyclonal antibody (1:2000) (Abcam, Cambridge, UK) was used. The next day, the primary antibody solution was removed; wash was performed twice with 0.3% triton X-100-PBS solution for 5 minutes; and then a secondary antibody solution [0.3% triton X-100-PBS solution, Alexa Fluor 488-labeled goat anti-rabbit IgG antibody (1:200) (Molecular Probes, Eugene, Oreg., USA)] was added, and reacted under shading at room temperature for 2 hours. After the reaction, the secondary antibody solution was removed, and the cells were washed twice with PBS for 5 minutes, stained for nuclei with DAPI staining, and then embedded with Aqua-Poly/Mount (Polysciences, Warrington, USA).

Using a fluorescent microscope (Cell Observer, Carl-Zeiss), images were taken from wells applied with the respective drug treatments using an object lens of 10× magnification. Using the image analysis software Meta-Morph (Molecular Devices, Tokyo), for those images, the length of MAP2-positive dendrites within the entire screen and the number of MAP2-positive neural cells within each image were measured and the length of dendrites per a neural cell was calculated.

Compared to Aβ25-35 untreated cells (Control), Aβ25-35-treated cells (Vehicle) significantly decreased in density of dendrites (FIG. 1). In contrast, with posttreatment with GPPGPAG (SEQ ID NO: 1) (10 nM), significant increase in density of dendrites was observed. In neither treatment with 1 nM nor 10 nM was any effect observed with GPPGPPG (SEQ ID NO: 2), GPPGPP (SEQ ID NO: 3), GPPGPA (SEQ ID NO: 4), PPGPAG (SEQ ID NO: 5), and GPP (FIG. 1).

[Quantitative Experiment for Presynaptic Density]

Five hours and 3 days after start of cell culture, the medium was all changed with a fresh medium containing B-27 supplement (Invitrogen) instead of equine serum. Then, medium change was repeated at a frequency of about once a week. 21 days after the start of culture, the pre-aggregated partial sequence fragment of amyloid beta (Aβ25-35) was added up to 10 μM at medium change. After another 3 days, the peptide or solvent was added when the medium was all change into a fresh one, and after another 4 days, immunostaining was performed.

Immunostaining for quantifying presynaptic density was performed as follows. After the end of the drug treatment term, the medium was removed and the cells were washed with PBS, loaded with a 4% paraformaldehyde (PFA, Wako Pure Chemical Co., Ltd)-PBS solution, left standing at room temperature for an hour, and fixed. Wash with 0.3% triton X-100 (Wako Pure Chemical Co., Ltd)-PBS solution for 5 minutes was performed twice. Then, a primary antibody solution [0.3% triton X-100-PBS solution, 1% normal goat serum (Wako Pure Chemical Co., Ltd), a primary antibody] was added, and reacted at 4° C. overnight.

For the primary antibody, murine anti-synatophysin monoclonal antibody (1:500) (Sigma-Aldrich Japan, Tokyo) and rabbit anti-MAP2 polyclonal antibody (1:2000) (Abcam, Cambridge, UK) were used. The next day, the primary antibody solution was removed; wash with 0.3% triton X-100-PBS solution for 5 minutes was performed twice; and then a secondary antibody solution [0.3% triton X-100-PBS solution, Alexa Fluor 594-labeled goat anti-mouse IgG antibody (1:200) (Molecular Probes, Eugene, Oreg., USA), and Alexa Fluor 488-labeled goat anti-rabbit IgG antibody (1:200) (Molecular Probes, Eugene, Oreg., USA)] were added, and reacted under shading at room temperature for 2 hours. After the reaction, the secondary antibody solution was removed, and the cells were washed twice with PBS for 5 minutes, stained for nuclei with DAPI staining, and then embedded in Aqua-Poly/Mount (Polysciences, Warrington, USA).

Using a fluorescent microscope (Cell Observer, Carl-Zeiss), images were taken from wells applied with the respective drug treatment using an object lens of 20× magnification. Using the image analysis software ImageJ (National Institutes of Health, Bethesda, USA), for those images, the length of MAP2-positive dendrites and the synaptophysin-positive area overlapping on the dendrites were measured and the synaptophysin-positive presynaptic area per a particular dendrite length was calculated.

Figure 2:
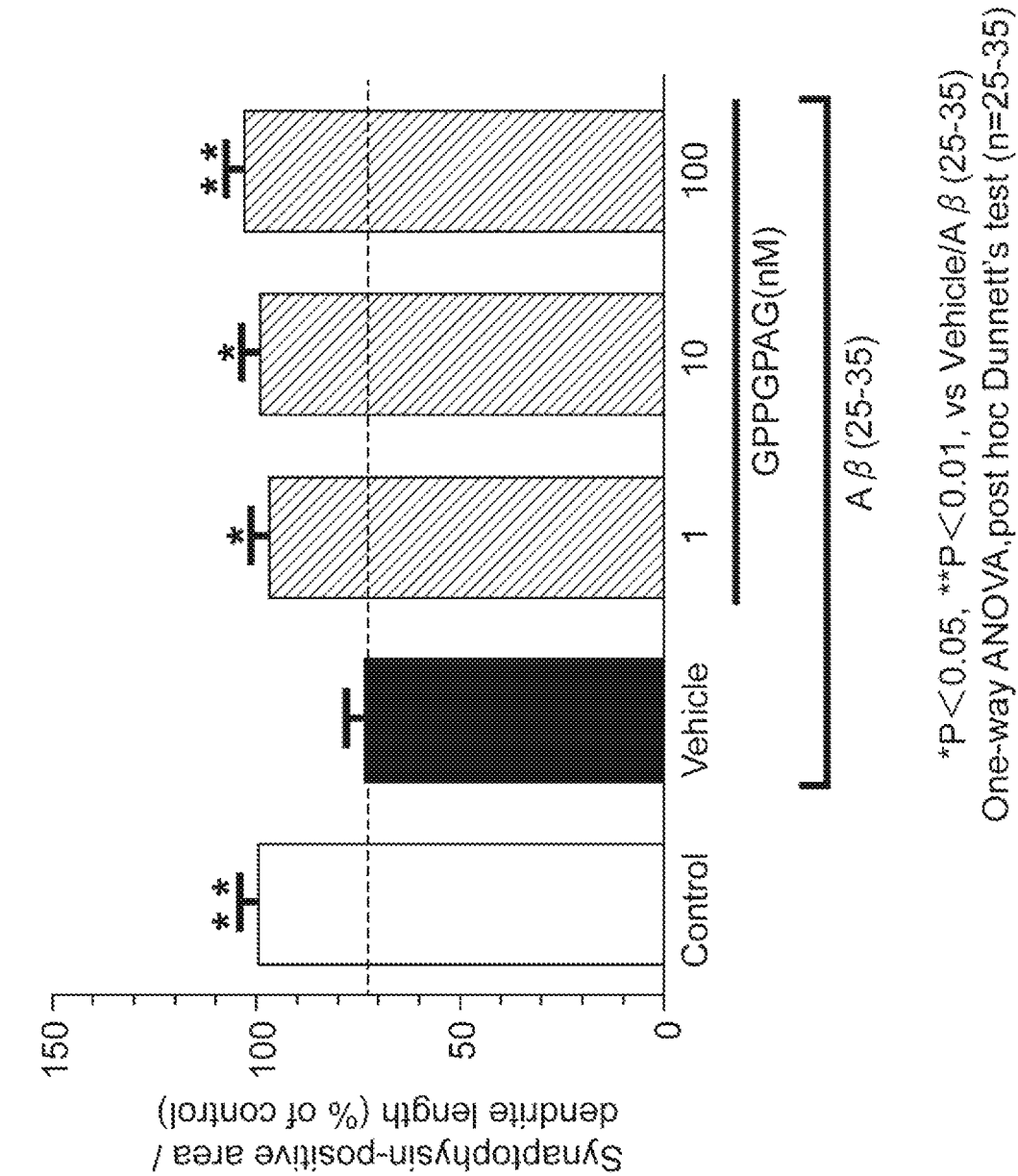
FIG. 2 is a diagram showing a change in presynaptic density on the dendrites with posttreatment with 1 nM, 10 nM, and 100 nM of GPPGPAG (SEQ ID NO: 1) in Aβ25-35-treated cells. "Control" indicates Aβ25-35 untreated cells, and "Vehicle" indicates Aβ25-35-treated cells treated with a simple solvent without the peptide. Asterisks indicate significant differences (*P<0.05, **P<0.01).

After a long-term culture for 21 days, Aβ25-35-treated cells (Vehicle) significantly decreased in presynaptic density on dendrites compared to Aβ25-35 untreated cells (Control) (FIG. 2). In contrast, with posttreatment with GPPGPAG (SEQ ID NO: 1), concentration-dependent increase in presynaptic density was observed. Particularly, significant increase was observed in 10 nM and 100 nM (FIG. 2).

[Object Recognition Memory Test]

GPPGPAG (SEQ ID NO: 1) was dissolved in an artificial cerebrospinal fluid, and an osmotic minipump model 1004 (ALZET Osmotic Pumps, Cupertino, USA) containing the solution inserted and fixed into the right lateral ventricle of each 5XFAD mouse to inject the solution into the lateral ventricle continuously for 28 days. The dosage was set such that GPPGPAG (SEQ ID NO: 1) would be constantly kept at 10 nM in the cerebrospinal fluid. Specifically, from a peptide flow of 0.11 μL/h from the pump and a production of cerebrospinal fluid of 18 μL/h in the mouse, the concentration of the peptide solution was calculated such that the peptide concentration in the murine cerebrospinal fluid would be kept at 10 nM (which was an effective concentration in the cell experiments), and the solution prepared thereby was loaded into the pump. As a comparative group, a group of 5XFAD mice was provided in which an osmotic minipump was similarly inserted and fixed into the right lateral ventricle of each 5XFAD mouse to continuously administer only an artificial cerebrospinal fluid (solvent-administered group). For these murine groups, object recognition memory test was performed.

Object recognition memory test is a test that employs a habit that an animal shows an interest for a new thing. In other words, this is a test for checking whether or not an object seen at a training stage is kept in memory at a test stage. The test was performed according to the description in references (Int J Neurosci, 121, pp. 181-190, 2011; and Int J Neurosci, 121, pp. 641-648, 2011). Specifically, it was performed as follows.

The test was performed in a room with relatively reduced lighting (about 100 lux). The appropriate time interval between the training stage and the testing stage was determined by preliminarily testing with another group of mice. There is no mark on the wall inside an open field box for testing. At the training stage, the same two objects are placed within the field, and exploratory behaviors for 10 minutes were allowed. At the testing stage, one of the objects is replaced with a new object but not changed in its position, and exploratory behaviors for 10 minutes were allowed. Increase in the number that the mice show interests for the new object replaced and take exploratory behaviors is defined as an index of object memory ability.

In the Example, the rate of the number of exploration for a new event to the total exploration time (%) was calculated as an exploratory preferential index.

Figure 3:
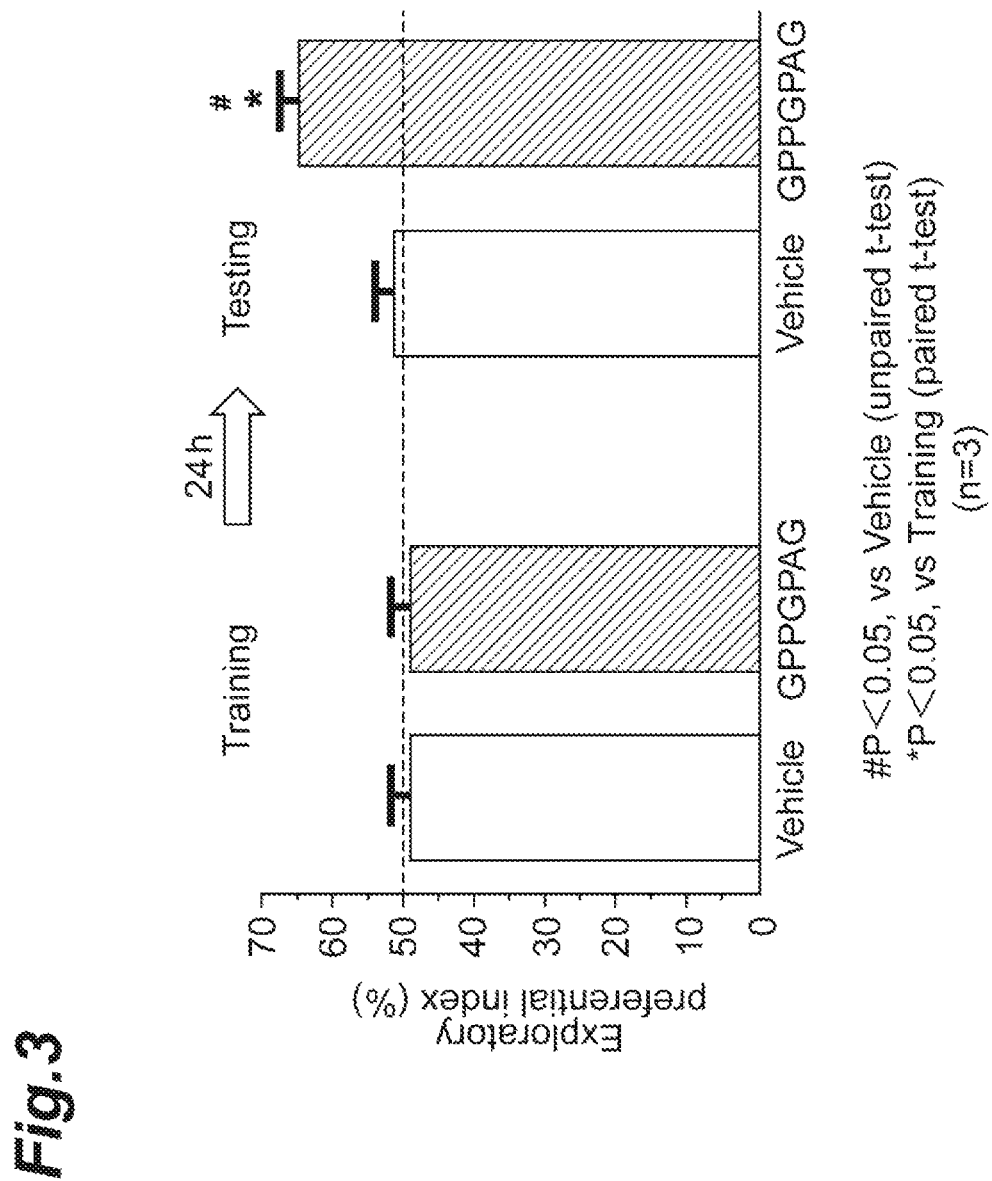
FIG. 3 is a diagram showing a change in exploratory preferential index with administration of GPPGPAG (SEQ ID NO: 1) in 5XFAD mice. "GPPGPAG" indicates a GPPGPAG (SEQ ID NO: 1)-administered group administered with GPPGPAG (SEQ ID NO: 1), and "Vehicle" indicates a solvent-administered group solely administered with a solvent without the peptide. Asterisks indicate significant differences (*P<0.05,#P<0.05).

In the Example, the interval between the training stage and testing stage was 24 hours. In the solvent-administered group of 5XFAD mice, there was no change in exploratory preferential index at the testing stage after 24 hours compared to the exploratory preferential index at the training stage (FIG. 3). This result showed that in the solvent-administered group of 5XFAD mice, the memory of the objects was not retained and memory disorder occurred. On the other hand, in the GPPGPAG (SEQ ID NO: 1)-administered group at the testing stage, exploratory preferential index significantly increased relative to the training stage (P<0.05), showing an amelioration of memory disorder (FIG. 3).

As described above, an effect for ameliorating memory disorder by the peptide consisting of the amino acid sequence of SEQ ID NO: 1 of the present invention has been shown.

What is claimed is:

1. A method of ameliorating memory impairment in a memory disorder caused by neuronal cell death or Aβ aggregation, comprising administering to a subject in need thereof a pharmaceutical composition comprising a peptide consisting of the amino acid sequence of SEQ ID NO: 1.

2. The method according to claim 1, wherein the memory disorder caused by neuronal cell death or Aβ aggregation is Alzheimer's disease.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: P1

<400> SEQUENCE: 1

Gly Pro Pro Gly Pro Ala Gly
1               5

<210> SEQ ID NO 2
<211> LENGTH: 7
<212> TYPE: PRT
<213> ORGANISM: Artificial Sequence
<220> FEATURE:
<223> OTHER INFORMATION: P2

<400> SEQUENCE: 2

Gly Pro Pro Gly Pro Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: P3

<400> SEQUENCE: 3

Gly Pro Pro Gly Pro Pro
1               5

<210> SEQ ID NO 4
<211> LENGTH: 6
<212> TYPE: PRT
<213> ORGANISM: Artificial Sequence
<220> FEATURE:
<223> OTHER INFORMATION: P4

<400> SEQUENCE: 4

Gly Pro Pro Gly Pro Ala
1               5
```

```
<210> SEQ ID NO 5
<211> LENGTH: 6
<212> TYPE: PRT
<213> ORGANISM: Artificial Sequence
<220> FEATURE:
<223> OTHER INFORMATION: P5

<400> SEQUENCE: 5

Pro Pro Gly Pro Ala Gly
1               5
```